(12) United States Patent
Brannan et al.

(10) Patent No.: US 9,192,426 B2
(45) Date of Patent: Nov. 24, 2015

(54) ABLATION DEVICE HAVING AN EXPANDABLE CHAMBER FOR ANCHORING THE ABLATION DEVICE TO TISSUE

(71) Applicant: Covidien LP, Mansfield, MA (US)

(72) Inventors: Joseph D. Brannan, Erie, CO (US); Gene H. Arts, Berthoud, CO (US)

(73) Assignee: Covidien LP, Mansfield, MA (US)

( * ) Notice: Subject to any disclaimer, the term of this patent is extended or adjusted under 35 U.S.C. 154(b) by 162 days.

(21) Appl. No.: 13/835,513

(22) Filed: Mar. 15, 2013

(65) Prior Publication Data

US 2013/0345699 A1 Dec. 26, 2013

Related U.S. Application Data

(60) Provisional application No. 61/664,586, filed on Jun. 26, 2012.

(51) Int. Cl.
| A61B 18/18 | (2006.01) |
| A61B 18/14 | (2006.01) |
| A61B 18/00 | (2006.01) |
| A61B 19/00 | (2006.01) |

(52) U.S. Cl.
CPC .............. *A61B 18/14* (2013.01); *A61B 18/1477* (2013.01); *A61B 18/1482* (2013.01); *A61B 2018/00023* (2013.01); *A61B 2018/00285* (2013.01); *A61B 2018/1425* (2013.01); *A61B 2019/5425* (2013.01)

(58) Field of Classification Search
CPC ........ A61B 18/04; A61B 18/12; A61B 18/14; A61B 18/1477; A61B 18/1482; A61B 2018/00023

USPC .............................................. 606/32, 41, 44
See application file for complete search history.

(56) References Cited

U.S. PATENT DOCUMENTS

| D223,367 | S | 4/1972 | Kountz |
| D263,020 | S | 2/1982 | Rau, III |
| D266,842 | S | 11/1982 | Villers et al. |
| D278,306 | S | 4/1985 | McIntosh |
| D295,893 | S | 5/1988 | Sharkany et al. |
| D295,894 | S | 5/1988 | Sharkany et al. |
| D354,218 | S | 1/1995 | Van de Peer |
| 5,507,802 | A | 4/1996 | Imran |

(Continued)

FOREIGN PATENT DOCUMENTS

| CN | 1103807 | 6/1995 |
| DE | 390937 | 3/1924 |

(Continued)

OTHER PUBLICATIONS

U.S. Appl. No. 08/136,098, filed Oct. 14, 1993, Roger A. Stern.

(Continued)

*Primary Examiner* — Christopher D Koharski
*Assistant Examiner* — Michael Carey (57) ABSTRACT

A surgical instrument is provided including a handle assembly, a shaft electrically coupled to the handle assembly and extending therefrom, an electrode assembly electrically coupled to the shaft for transmitting energy to tissue to treat tissue, and a chamber defined in the shaft and positioned proximal a distal end thereof and configured to selectively expand. The expansion of the chamber anchors the surgical instrument to the tissue.

17 Claims, 4 Drawing Sheets

(56) References Cited

U.S. PATENT DOCUMENTS

| | | | |
|---|---|---|---|
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,595,989 B1 | 7/2003 | Schaer | |
| 6,623,480 B1 | 9/2003 | Kuo et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,881,807 B2 | 2/2011 | Schaer | |
| D634,010 S | 3/2011 | DeCarlo | |
| 8,038,674 B2 | 10/2011 | Schmaltz | |
| 8,043,288 B2 | 10/2011 | Dando et al. | |
| 8,359,082 B2 | 1/2013 | Selkee | |
| 8,361,097 B2 | 1/2013 | Patel et al. | |
| 2002/0183742 A1 | 12/2002 | Carmel et al. | |
| 2003/0135117 A1 | 7/2003 | Ward et al. | |
| 2004/0172110 A1* | 9/2004 | Satake | 607/101 |
| 2004/0230111 A1 | 11/2004 | Smith et al. | |
| 2007/0073285 A1* | 3/2007 | Peterson | 606/41 |
| 2009/0005769 A1 | 1/2009 | Haywood | |
| 2009/0018533 A1 | 1/2009 | Perkins et al. | |
| 2009/0299355 A1* | 12/2009 | Bencini et al. | 606/21 |
| 2010/0286528 A1 | 11/2010 | Davis et al. | |
| 2011/0276047 A1 | 11/2011 | Sklar et al. | |
| 2012/0059286 A1* | 3/2012 | Hastings et al. | 601/2 |
| 2012/0108953 A1* | 5/2012 | Markowitz et al. | 600/424 |
| 2012/0310065 A1 | 12/2012 | Falwell et al. | |
| 2013/0030424 A1 | 1/2013 | Merryman et al. | |
| 2013/0060247 A1 | 3/2013 | Sklar et al. | |
| 2013/0060248 A1 | 3/2013 | Sklar et al. | |
| 2013/0158390 A1 | 6/2013 | Tan et al. | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 102 17 281 A1 | 10/2003 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| EP | 1297795 A1 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001003776 | 1/2001 |
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO00/36985 | 6/2000 |
| WO | 00/59394 A1 | 10/2000 |
| WO | 02/056772 A2 | 7/2002 |
| WO | WO2010/035831 | 4/2010 |

OTHER PUBLICATIONS

U.S. Appl. No. 08/483,742, filed Jun. 7, 1995, Roger A. Stern.
U.S. Appl. No. 13/236,997, filed Sep. 20, 2011, Behnke, II et al.
U.S. Appl. No. 13/237,068, filed Sep. 20, 2011, Behnke, II et al.
U.S. Appl. No. 13/237,187, filed Sep. 20, 2011, Behnke, II et al.
U.S. Appl. No. 13/237,342, filed Sep. 20, 2011, Behnke, II et al.
U.S. Appl. No. 13/237,488, filed Sep. 20, 2011, Behnke, II et al.
U.S. Appl. No. 13/343,788, filed Jan. 5, 2012, William O. Reid Jr.
U.S. Appl. No. 13/343,798, filed Jan. 5, 2012, William O. Reid Jr.
U.S. Appl. No. 13/344,753, filed Jan. 6, 2012, Lee et al.
U.S. Appl. No. 13/344,790, filed Jan. 6, 2012, Lee et al.
U.S. Appl. No. 13/358,129, filed Jan. 25, 2012, Brannan.
U.S. Appl. No. 13/400,223, filed Feb. 20, 2012, Anthony B. Ross.

(56) References Cited

OTHER PUBLICATIONS

U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/657,270, filed Oct. 22, 2012, Brannan.
U.S. Appl. No. 13/657,609, filed Oct. 22, 2012, Prakash.
U.S. Appl. No. 13/657,638, filed Oct. 22, 2012, Brannan.
U.S. Appl. No. 13/681,741, filed Nov. 20, 2012, Steven Kim.
U.S. Appl. No. 13/711,067, filed Dec. 11, 2012, Brannan.
U.S. Appl. No. 13/711,086, filed Dec. 11, 2012, Brannan.
U.S. Appl. No. 13/711,164, filed Dec. 11, 2012, Brannan.
U.S. Appl. No. 13/734,638, filed Jan. 4, 2013, Bonn.
U.S. Appl. No. 13/740,706, filed Jan. 14, 2013, Rossetto.
U.S. Appl. No. 13/740,754, filed Jan. 14, 2013, Prakash.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic (g) Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul., 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.

Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™ " Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J .MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. Of Laser Medicine & Dept. Of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799801.
Herman at al., "Laparoscopic Intestinal Resection With the LigaSure™ Vessel Sealing System: A Case Report" Innovations That Work, Feb. 2002.
Humphries Jr. et al., "Finite Element Codes to Model Electrical Heating and Non•Llnear Thermal Transport in Biological Media", Proc. ASME HTD-355, 131 (1997).
Ian D. McRury et al., the Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.

(56) References Cited

OTHER PUBLICATIONS

Joseph G. Andriole M.D. et al., "Biopsy Needle Characteristics Assessed in the Laboratory", Radiology 148: 659-662, Sep. 1983.
Joseph Ortenberg, " LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192—Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'L Federation of Gynecology and Obstetrics FIGO World Congress 2000, Washington, DC.
MDTECH product literature (Dec. 1999) "FlexStrand": product description, 1 page.
Mdtech product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al,, "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (1 PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. On Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: Targis™ Technology , "Overcoming the Challenge" located at: <http://www.urologix.com-!medicaUtechnology.html >Nov. 18, 1999; 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
Copy of International Search Report from PCT Application No. PCT/US2013/044754 mailed Sep. 2, 2013.

\* cited by examiner

ABLATION DEVICE HAVING AN EXPANDABLE CHAMBER FOR ANCHORING THE ABLATION DEVICE TO TISSUE

CROSS REFERENCE TO RELATED APPLICATION

The present application claims the benefit of and priority to U.S. Provisional Application Ser. No. 61/664,586, filed on Jun. 26, 2012, the entire contents of which are incorporated herein by reference.

BACKGROUND

1. Technical Field

The present disclosure relates to surgical instruments and, more particularly, to an electrosurgical ablation device utilizing a limited-use component, such as a disposable needle, and having an expandable chamber for anchoring the ablation device to tissue.

2. Background of Related Art

Energy-based tissue treatment is well known in the art. Various types of energy (e.g., electrosurgical, ultrasonic, microwave, cryogenic, thermal, laser, etc.) are applied to tissue to achieve a desired result, e.g., to cut, ablate, coagulate, and/or seal tissue.

Electrosurgery involves the application of radio frequency (RF) or microwave energy to a surgical site to cut, ablate, coagulate, and/or seal tissue. In monopolar electrosurgery, a source or active electrode, which is typically part of the surgical instrument held by the surgeon, delivers RF electrical current from a generator to tissue, while a patient return electrode is placed remotely from the active electrode to carry the current back to the generator.

In tissue ablation electrosurgery, for example, the RF or microwave energy may be delivered to targeted tissue by a limited-use component, such as a probe, needle, or electrode assembly. More specifically, with respect to the use of a needle, the needle is typically advanced through tissue to a desired position either prior to or during application of energy to tissue. After repeated use, these needles may become dull, bent, or otherwise deformed and, consequently, may become more difficult to place and operate upon subsequent use. As such, ablation devices have been developed which include replaceable needles, thus allowing the needle to be replaced after one or more uses without requiring replacement of the entire device (e.g., the handpiece).

During electrosurgery it is typically desirable to position the probe, needle or electrode assembly adjacent to tissue to be ablated and maintain the same position for a period of time necessary to ablate the tissue.

SUMMARY

As used herein, the term "distal" refers to the portion that is being described which is further from a user, while the term "proximal" refers to the portion that is being described which is closer to a user. Further, to the extent consistent with one another, any of the aspects described herein may be used in conjunction with any of the other aspects described herein.

In accordance with aspects of the present disclosure, a surgical instrument is provided generally including a reusable component and a limited-use component releasably engagable to a shaft extending from the reusable component. In embodiments, the surgical instrument is an ablation device. An expandable chamber is positioned along the shaft and is in fluid communication with a fluid source. The fluid source enables the delivery of a fluid to the chamber causing the chamber to expand. It is desirable that the fluid is delivered to the chamber when the limited-use component is placed in target tissue and is ready for performing an ablation procedure.

The expandable chamber anchors or locks the surgical instrument and prevents the surgical instrument from moving or shifting during a surgical procedure, such as a tissue ablation procedure. The expandable chamber maintains the limited-use component's location in the target anatomy post placement despite patient respiration, patient muscular-skeletal movement, CT gantry movement, movement due to leverage on the surgical instrument from cables/fluid tubing, etc.

Additionally, the expandable chamber improves visibility of the surgical instrument and the limited-use component, such as a needle, under ultrasound imaging, e.g., ultrasonography, due to the hyper- or hypo-echoic enhancement offered from the fluid used. Gas (such as carbon dioxide) would be hyper-echoic; liquid (such as saline or water) would be hypo-echoic. The visibility due to ultrasound imaging can be used to designate radiation section location during the imaging process.

In accordance with an aspect of the present disclosure, a surgical instrument is provided and includes a handle assembly configured to connect to a source of energy; a shaft electrically coupled to the handle assembly and extending therefrom; an electrode assembly electrically coupled to the shaft for transmitting energy to tissue to treat tissue, and a chamber defined in the shaft and positioned proximal a distal end thereof and configured to selectively expand. Expansion of the chamber anchors the surgical instrument to the tissue. The handle assembly is a reusable handle assembly and the electrode assembly is a limited-use electrode assembly. The chamber is in fluid communication with a fluid source. The fluid delivered to the chamber from the fluid source expands the chamber. That is, the chamber is movable from a non-expanded position in which the chamber is flush with the shaft to an expanded position.

The fluid source can be a cooling fluid source that stores fluid used to cool the electrode assembly during operation of the surgical instrument. The shaft includes at least one lumen in fluid communication with the chamber. The fluid is selected from the group consisting of a gas and a liquid.

The surgical instrument can further include an inlet port defined in the handle assembly in fluid communication with the chamber. The electrode assembly includes a needle having a distal end configured to penetrate tissue.

The surgical instrument can further include an inlet port in fluid communication with the chamber. The inlet port can include a luer connector. An outer surface of the chamber can include a plurality of protrusions. The chamber can be made from at least one polymer material. The surgical instrument can be an ablation device.

According to another aspect of the present disclosure, a surgical instrument is provided and includes a reusable handle assembly configured to connect to a source of energy; and a shaft electrically coupled to the reusable handle assembly and extending from the reusable handle assembly. The shaft includes a connection mechanism. The surgical instrument further includes a limited-use component configured to connect to the connection mechanism of the shaft for mechanically engaging and electrically coupling the shaft and the limited-use component for transmitting energy to treat tissue. The surgical instrument further includes an expandable chamber positioned on the shaft. The expandable chamber is in fluid communication with a fluid source that is configured to selectively deliver fluid to the expandable chamber for expanding the expandable chamber to anchor the surgical instrument to tissue.

The fluid source can be a cooling fluid source that stores fluid used to cool the limited-use component during operation of the surgical instrument. The shaft includes at least one lumen defined therein in fluid communication with the expandable chamber. The fluid is selected from the group consisting of a gas and a liquid. The limited-use component can include a needle having a distal end configured to penetrate tissue.

The surgical instrument can further include an inlet port defined in the handle assembly. The inlet port is in fluid communication with the expandable chamber. The inlet port can include a luer connector. The fluid source can be a syringe configured for connection to the luer connector.

In a further aspect of the present disclosure, a method is provided for anchoring an ablation device to tissue. The method includes positioning an electrode assembly of the ablation device within tissue to be ablated; and expanding a chamber proximally located from the electrode assembly on a shaft of the ablation device. The expanded chamber anchors the ablation device to tissue.

BRIEF DESCRIPTION OF THE DRAWINGS

Various aspects of the present disclosure are described herein with reference to the drawings wherein like reference numerals identify similar or identical elements.

DETAILED DESCRIPTION

In accordance with the present disclosure, there is provided an electrosurgical instrument, such as an electrosurgical ablation device, having a reusable component. The reusable component includes a handle assembly and a shaft extending therefrom. The handle assembly may include an inlet port that connects to a fluid source for delivering fluid via a conduit assembly from the handle assembly through the shaft to an anchoring mechanism having an expandable chamber. The anchoring mechanism is positioned proximally from a distal end of the shaft. Alternatively, the fluid source, such as a cooling fluid source, may be connected to the shaft.

A limited-use component is releasably connected or engaged to the distal end of the shaft. The limited-use component can be an ablation probe, an ablation needle, or an electrode assembly. In embodiments described herein, for exemplary purposes, the limited-use component is referred to as a needle electrode assembly and is configured for delivering energy to tissue, such as RF energy.

The fluid delivered to the expandable chamber of the anchoring mechanism can be a gas or a liquid. The fluid is used to expand the expandable chamber from a non-expanded position in which the chamber is flush with an outer surface of the shaft to an expanded position. In the expanded position, the expandable chamber can anchor the ablation device in proximity to target tissue prior to an ablation procedure. That is, prior to the ablation procedure, the ablation needle is inserted into target tissue. Fluid is then delivered to the expandable chamber to expand the chamber and anchor or lock the surgical instrument to tissue in proximity to the target tissue. The expandable chamber maintains the limited-use component's location in the target anatomy post placement despite patient respiration, patient muscular-skeletal movement, CT gantry movement, movement due to leverage on the surgical instrument from cables/fluid tubing, etc.

The expandable chamber also improves visibility of the surgical instrument and the limited-use component, such as a needle, under ultrasound imaging, e.g., ultrasonography, due to the hyper- or hypo-echoic enhancement offered from the fluid used. Gas (such as carbon dioxide) would be hyperechoic; liquid (such as saline or water) would be hypo-echoic. The visibility due to ultrasound imaging can be used to designate a radiation section location during the imaging process.

Referring to FIGS. 1-7C, an electrosurgical ablation system provided in accordance with the present disclosure is shown generally designated by reference numeral 10. Although ablation system 10 is shown configured as an RF-ablation system 10, the present disclosure is equally applicable for use with microwave ablation systems, or any other suitable surgical system including single-use or limited-use disposable components. Obviously, different considerations apply depending on the particular device and/or system used; however, the novel aspects with respect to the anchoring of ablation device 100 of ablation system 10 to tissue remains generally consistent regardless of the particular type of device and/or system used. For the purposes herein, ablation system 10 is generally described.

Continuing with reference to FIGS. 1-7C, surgical instrument or ablation device 100 of ablation system 10 generally includes a handle assembly 110 and a needle electrode assembly 150 releasably engagable with and extending from a shaft 130 of handle assembly 110. Although only one needle electrode assembly 150 is shown, additional needle electrode assemblies, either similar to or different from needle electrode assembly 150, may be provided for releasable engagement with handle assembly 110. As such, a desired needle electrode assembly may be selected and engaged to handle assembly 110, depending on a particular purpose and/or to replace a "spent" needle. Shaft 130 may be a composite material, such as Polyglass composite tubing, and/or a fiber glass material.

Handle assembly 110 includes a housing 112 which may be ergonomically or otherwise configured to facilitate the grasping and manipulation of housing 112 by a user to position needle electrode assembly 150 as desired. Housing 112 is formed from an insulative material and defines proximal and distal ends 113, 115, respectively. Proximal end 113 of housing is configured to receive one or more lines 22a, 22b from an energy source, e.g., generator (not shown), and cooling fluid source (not shown), respectively, for supplying energy and cooling fluid, respectively, to needle electrode assembly 150. Shaft 130 extends from distal end 115 of housing 112.

An anchoring mechanism 200, as further described below, includes an expandable chamber 210 for anchoring the ablation device 100 to tissue in proximity to target tissue to be ablated. Expandable chamber 210 can be manufactured through adhesion of a cylinder of thin polymer around shaft 130. PET or FEP may be material choices for expandable chamber 210, as well as materials common to angioplasty balloons, or materials whose expansion size is limited.

A connection mechanism (not shown) is provided at a distal end 135 of shaft 130 and is configured for connecting shaft 130 to needle electrode assembly 150 for releasably engaging needle electrode assembly 150 and shaft 130 to one another. In embodiments, connection mechanism provides a friction-fit engagement between shaft 130 and needle electrode assembly 150 to releasably mechanically engage needle electrode assembly 150 and shaft 130 to one another. Other releasable connection mechanisms, e.g., snap-fit engagements, are also contemplated.

In embodiments, the connection mechanisms include one or more electrical contact pins (not shown) extending distally from shaft 130 and configured for insertion into a proximal end of needle electrode assembly 150 to establish electrical communication between shaft 130, handle assembly 110 and needle electrode assembly 150 upon mechanical engagement of shaft 130 and needle electrode assembly 150.

One or more wires (not explicitly shown) extending through housing 112 of handle assembly 110 couple the one or more electrical contact pins to line 22 which extends proximally from housing 112 of handle assembly 110 ultimately coupling the ablation device 100 to the generator (not shown). As such, power and/or control signals may be transmitted between the generator and needle electrode assembly 150.

Figure 7A:
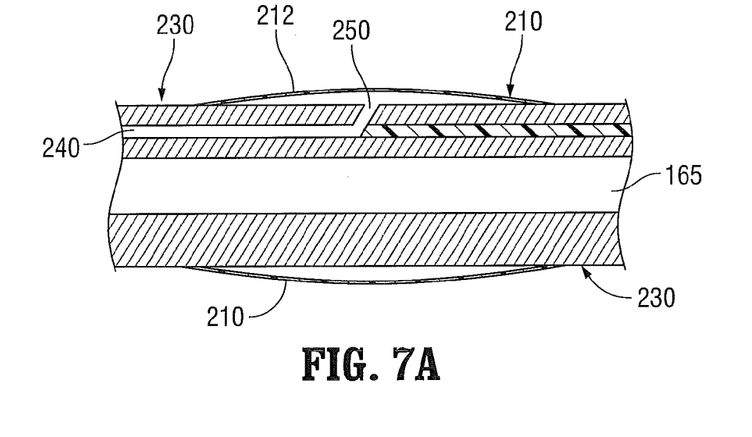
FIG. 7A is a cross-sectional view of the ablation device showing a conduit for delivering fluid to the expandable chamber in the expanded position in accordance with the present disclosure.

In particular, the one or more contact pins may be configured for establishing a conductive path for transmission of energy between generator and needle 170 of needle electrode assembly 150. As such, upon activation, energy can be transmitted from the generator to needle electrode assembly 150 and, ultimately, conducted through tissue to ablate or otherwise treat tissue. One or more lumens 165 extending through the one or more contact pins and shaft 130 (see FIG. 7) may also be provided for circulation of cooling fluid from a cooling fluid source (not shown) through shaft 130 and a hollow interior of needle 170.

The one or more contact pins (or other electrical contacts (not shown)) may additionally or alternatively be utilized for identifying or verifying the identification of the particular type of needle electrode assembly 150 engaged with shaft 130. This feature helps ensure that an acceptable needle electrode assembly 150 is engaged to shaft 130 and/or that the proper energy delivery and control parameters for the particular needle electrode assembly 150 engaged with shaft 130 are provided by the generator.

Further, the operation of the cooling fluid source (not shown) may also be at least partially dependent upon the particular type of needle electrode assembly 150 detected. Thus, identifying information for the particular type of needle electrode assembly 150 engaged to shaft 130 may be relayed to and utilized by the cooling fluid source for controlling the supply of cooling fluid to the needle electrode assembly 150 in accordance therewith. Other configurations of contact(s) or similar features for establishing electrical communication and electrical energy transmission between shaft 130, handle assembly 110 and needle electrode assembly 150 are also contemplated.

Needle 170 extends distally from shaft 130 to distal end 176 thereof, which defines a distal tip 178 configured to facilitate the penetration of tissue while minimizing the risk of hemorrhage from the puncture tract, although other distal tip configurations are also contemplated. Needle 170 is formed from an electrically-conductive material of which at least distal end 176 is exposed. An insulative sleeve may be disposed about a portion of needle 170 such that at least distal end 176 of needle 170 is exposed. With distal end 176 of needle 170 exposed, energy, e.g., RF energy, can be delivered from needle 170 to surrounding tissue to treat, e.g., ablate, tissue.

As mentioned above, an energy source, e.g., generator, is provided for providing power and/or control signals to needle electrode assembly 150 via an electrical line(s) and one or more contact pins.

Circulation of the cooling fluid to needle electrode assembly 150 may be established through the use of a pump (not shown) or other suitable mechanism disposed within housing 112 of handle assembly 110, or the pump (not shown) may be externally disposed.

Figure 1:
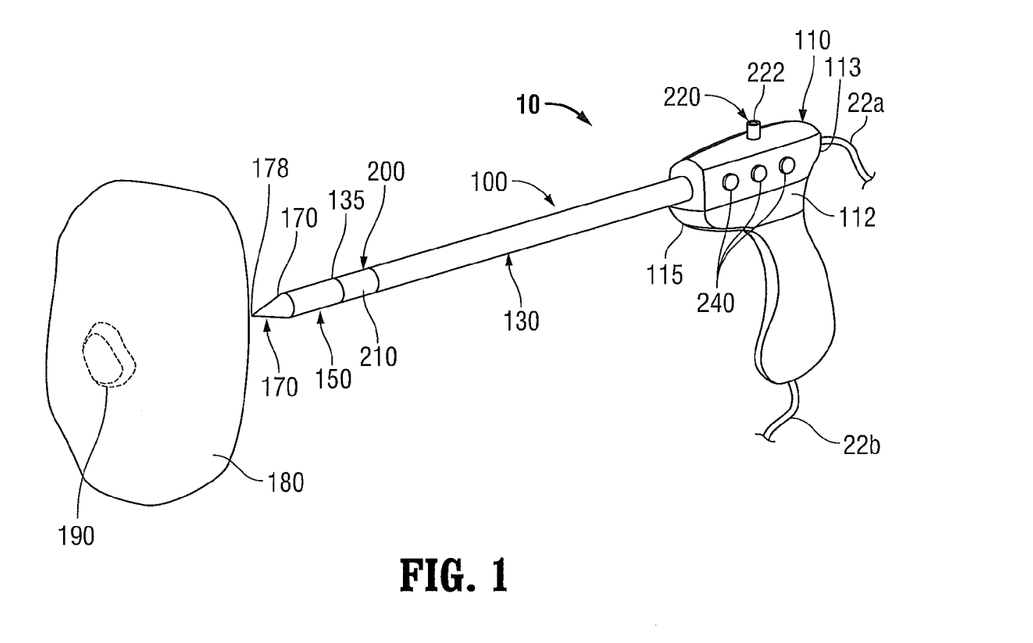
FIG. 1 is a perspective view of an electrosurgical ablation device of an electrosurgical system provided in accordance with the present disclosure in proximity to target tissue to be ablated.
Figure 2:
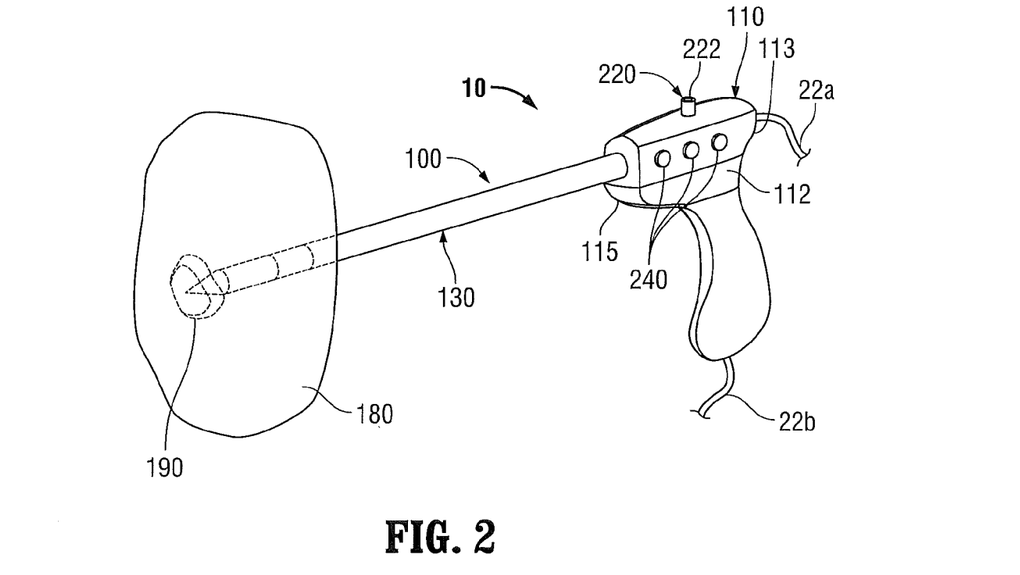
FIG. 2 is a perspective view of the ablation device of FIG. 1 with an ablation needle positioned within the target tissue in accordance with the present disclosure.

In operation, as shown by FIGS. 1 and 2, ablation device 100, led by distal tip 178 of needle 170, is inserted into an operative site such that exposed distal end 176 of needle 170 of ablation device 100 is positioned adjacent to or within target tissue 190 (such as a tumor within the liver) to be treated, e.g., ablated. A return pad or return electrode (not shown) may, at this point or prior to, be operatively-adhered to or connected to the patient. With exposed distal end 176 of needle 170 in position, as determined by any suitable imaging procedure, fluid is delivered to expandable chamber 210 of anchoring mechanism 200 via an inlet port 220 of handle assembly 110. Inlet port 220 can have or be fitted with a luer connector 222 configured for receiving a syringe 230. Other fluid sources, including the cooling fluid source (not shown) can be used for delivering fluid to expandable chamber 210 when a pump (not shown) is turned on and could be deflated by turning the pump off.

The fluid can be a gas (such as, for example, air or carbon dioxide) or liquid (such as, for example, saline or water) which is delivered through inlet port 220 of handle assembly 110 by syringe 230 or other device, including connecting a fluid source to inlet port 220, such as a cooling fluid source or faucet. Inlet port 220 is in fluid communication with expandable chamber 210 via a conduit assembly 230. With reference to FIG. 7A which is an enlarged view of the anchoring mechanism 200 and its expandable chamber 210, conduit assembly 230 includes at least one conduit or lumen 240 in fluid communication with inlet port 220 and extending to a point proximal to distal end 135 of shaft 130. Conduit 240 defines an opening 250 for delivering the fluid to expandable chamber 210.

In embodiments, expandable chamber 210, or balloon, expands for increasing the diameter of shaft 130 minimally, such as from about 0.094 to 0.100 inch, to effectively anchor needle electrode assembly 150 to tissue 180. That is, during expansion, chamber 210 effectively increases the diameter of shaft 130, thereby causing chamber 210 to push against surrounding tissue for anchoring ablation device 100 to the tissue. The small amount of expansion of chamber 210 allows for tissue 180 to comply with expandable chamber 210 without risk of hemorrhage.

The lumen 240 within shaft 130 may extend the full length of shaft 130 for fabrication ease, and then it may be potted with epoxy or other material from distal end 135 proximally up to the desired location for chamber 210. Opening 250 may be created with simple machining to connect lumen 240 with the interior of chamber 210.

Figure 7B:
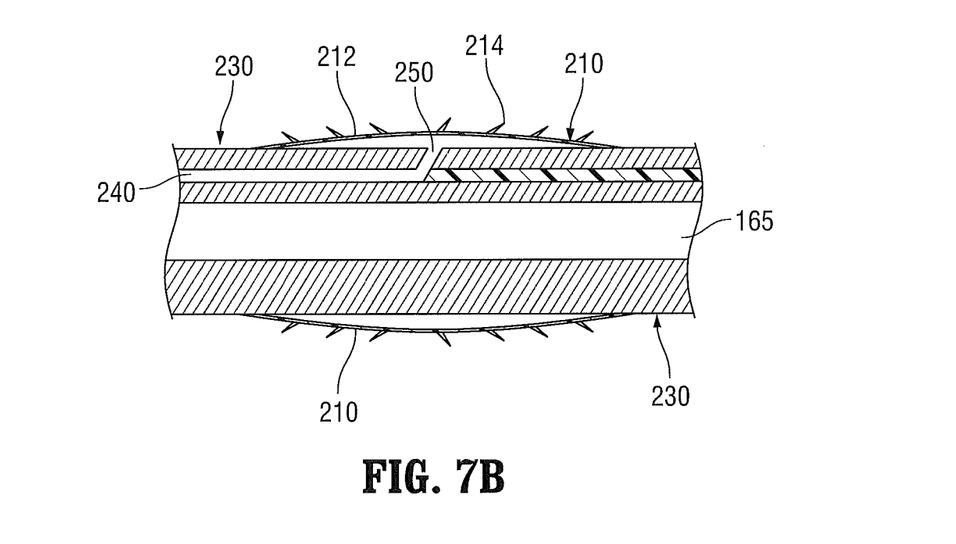
FIG. 7B is a cross-sectional view of the ablation device as in FIG. 7A with an outer surface of expandable chamber having structures for aiding in the anchoring of ablation device to tissue in accordance with present disclosure.
Figure 7C:
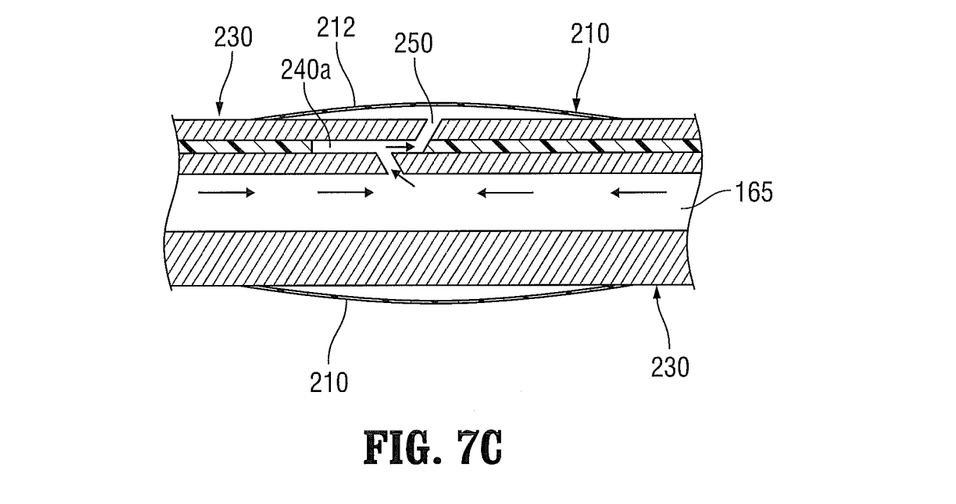
FIG. 7C is a cross-sectional view of an alternate ablation device in accordance with the present disclosure.

In an alternate embodiment as shown by FIG. 7C, lumen 240a is in fluid communication with the interior of chamber 210 and lumen 165 extending through shaft 130. In this embodiment, cooling fluid flowing to needle electrode assembly 150 via lumen 165 creates back pressure (shown by the arrows pointing to the left) within lumen 165. The back pressure causes the fluid to flow via opening 168 to lumen 240 and to the interior of chamber 210 via opening 250 to fill the chamber 210 with fluid.

Figure 3:
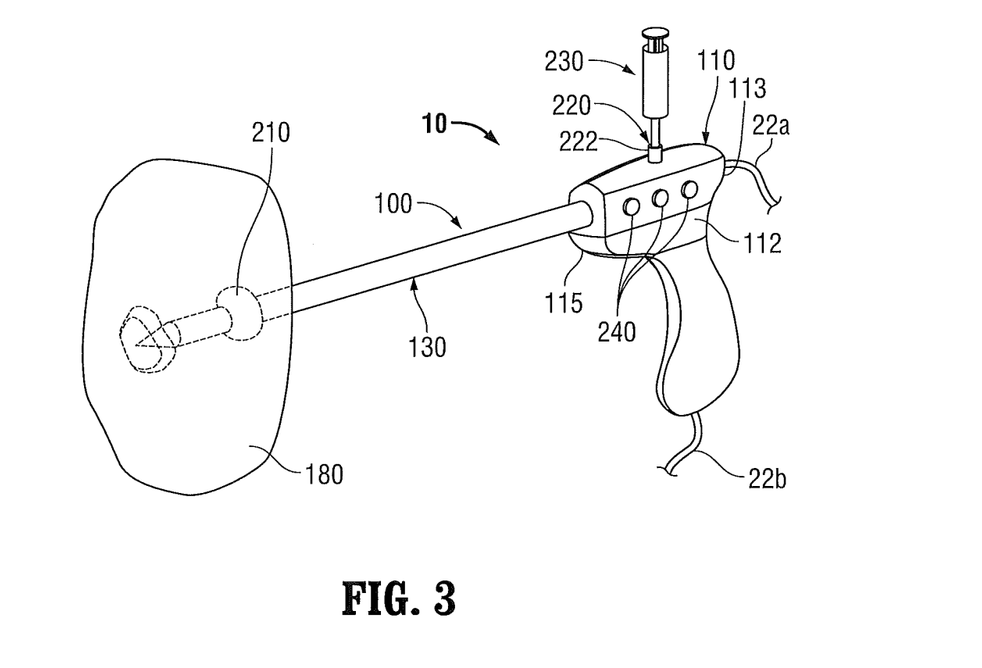
FIG. 3 is a perspective view of the ablation device of FIG. 1 showing an expandable chamber in the expanded position anchoring the ablation device to tissue in proximity to the target tissue in accordance with the present disclosure.
Figure 4:
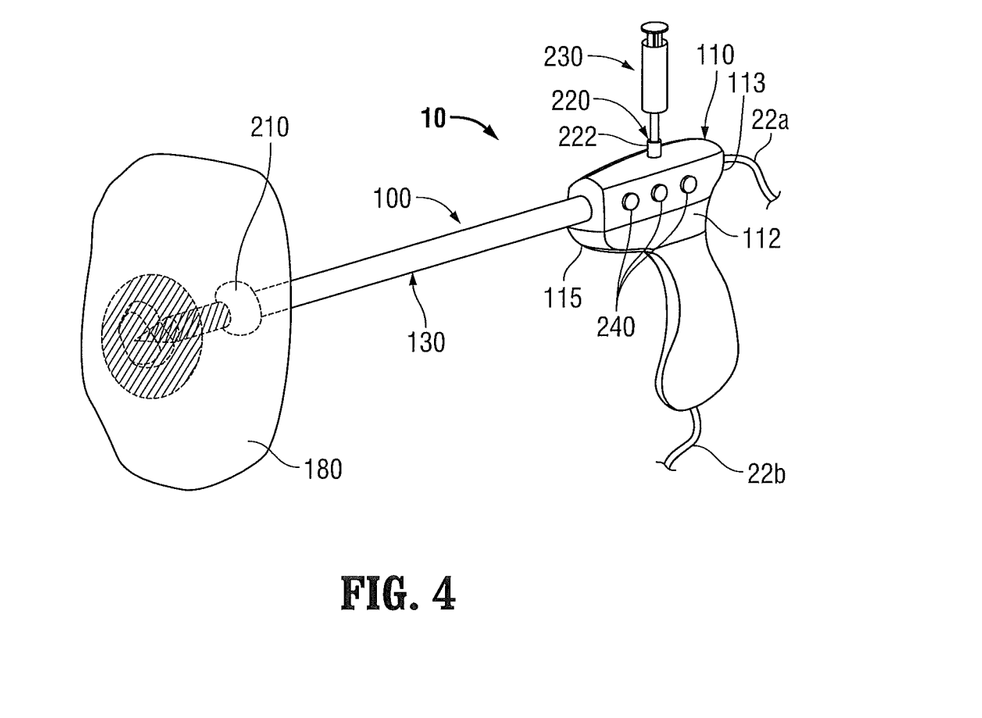
FIG. 4 is a perspective view of the ablation device ablating the target tissue while the expandable chamber prevents the ablation device from moving during the ablation procedure in accordance with the present disclosure.
Figure 5:
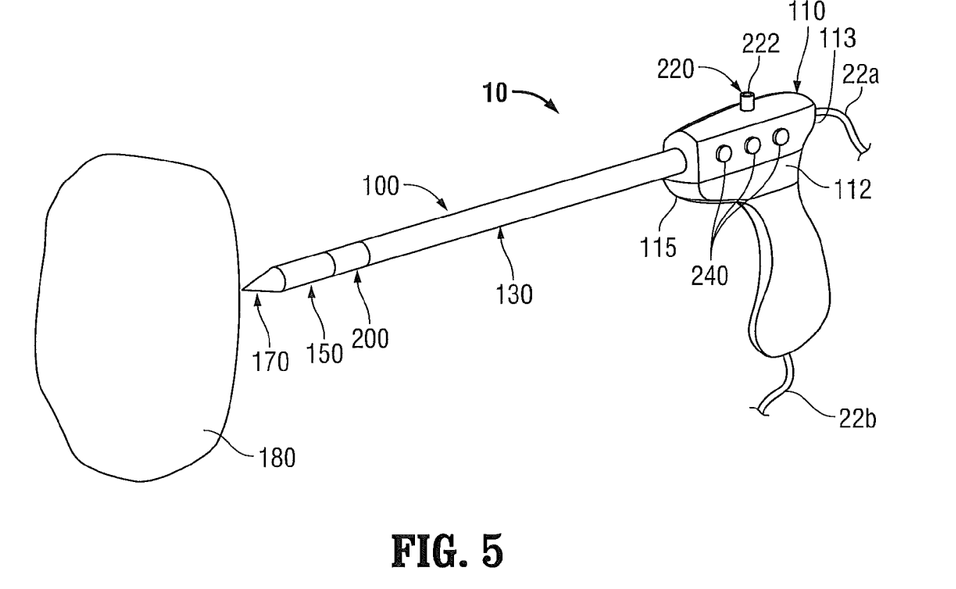
FIG. 5 is a perspective view of the ablation device removed from the tissue with the expandable chamber in the non-expanded position following the ablation procedure in accordance with the present disclosure.
Figure 6:
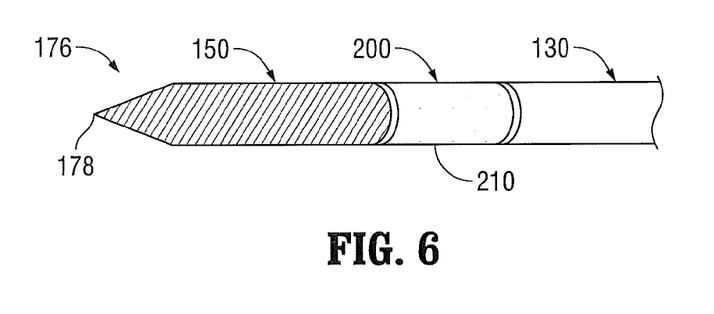
FIG. 6 is an enlarged view of the distal end of the ablation device showing an ablation needle and the expandable chamber in the non-expanded position in accordance with present disclosure.

In either embodiment, upon fluid entering chamber 210, the fluid circumferentially expands chamber 210 from a non-expanded position to an expanded position. In the non-expanded position, as shown by FIGS. 1 and 2, the chamber 210 is flush with an outer surface of shaft 130. In the expanded position, as shown by FIGS. 3 and 4, expandable chamber 210 presses against tissue 180 in proximity to target tissue 190 for anchoring or locking ablation device 100 to tissue 180. In embodiments, as shown by FIG. 7B, an outer surface 212 of chamber 210 includes structures 214, such as protrusions, for biting into tissue 180 as chamber 210 expands for further aiding in the anchoring of ablation device 100 to tissue 180.

Ultrasonography may be utilized to determine whether the ablation device 100 is correctly positioned, with exposed distal end 176 of needle 170 through target tissue 190. The expandable chamber 210 in the expanded position improves visibility of the ablation device 100 and the needle 170 under ultrasound imaging, e.g., ultrasonography, due to the hyper- or hypo-echoic enhancement offered from the fluid used. Gas (such as carbon dioxide) would be hyper-echoic; liquid (such as saline or water) would be hypo-echoic. The visibility due to ultrasound imaging can be used to designate the radiation section location during the imaging process. The visibility due to ultrasound imaging can also be used to determine whether to reposition needle 170 of ablation device 100.

If ablation device 100 is determined to be correctly positioned, energy, e.g., RF energy, is then delivered from the generator (not shown) to needle 170 and is conducted from exposed distal end 176 of needle 170 through the target tissue, ultimately to be collected by the return electrode (not shown). The use of microwave energy is also contemplated. An effective amount of energy at an effective energy level and for an effective duration of time is delivered to tissue to achieve the desired result, e.g., to treat the target tissue. To this end, one or more control switches and/or buttons 240 may be provided on handle assembly 110 for controlling the supply of energy to needle 170, or, alternatively, the supply of energy may be automatically or manually controlled by the generator (not shown).

Either prior to or simultaneously with the delivery of electrosurgical energy to needle 170, the cooling fluid provided by the cooling fluid source (not shown) may be circulated through a hollow interior of needle 170 to withdraw heat from needle 170, thus maintaining needle 170 in a relatively cooled state during use. The delivery of cooling fluid to the hollow interior of needle 170 may likewise be controlled by one or more control switches (not shown) disposed on handle assembly 110, or via cooling fluid source (not shown) itself.

At the completion of the procedure, expandable chamber 210 is returned to the non-expanded position by withdrawing fluid within chamber 210. The fluid can be withdrawn from inlet port 220 by connecting a vacuum or aspirator. With chamber 210 in the non-expanded position, ablation device 100 is unlocked from tissue 180 enabling removal of shaft 130 and needle electrode assembly 150 from the patient.

Needle electrode assembly 150 may be disengaged from handle assembly 110 and both may be sterilized for reuse. Ultimately, needle electrode assembly 150 may be re-engaged to handle assembly 110 (or may be engaged to another handle assembly) for subsequent use.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument comprising:
   a handle assembly configured to connect to a source of energy;
   a shaft electrically coupled to the handle assembly and extending therefrom;
   an electrode assembly electrically coupled to the shaft for transmitting energy to tissue to treat tissue, the electrode assembly having a proximal end configured to releasably couple to a distal end of the shaft and forming a distal tip configured to penetrate tissue; and
   a chamber disposed on the shaft proximal to the electrode assembly, the chamber configured to selectively expand, wherein expansion of the chamber anchors the surgical instrument to the tissue.

2. The surgical instrument according to claim 1, wherein the handle assembly is a reusable handle assembly, and wherein the electrode assembly is a limited-use electrode assembly.

3. The surgical instrument according to claim 1, wherein the chamber is in fluid communication with a fluid source, and wherein fluid delivered to the chamber from the fluid source expands the chamber.

4. The surgical instrument according to claim 3, wherein the fluid source stores cooling fluid.

5. The surgical instrument according to claim 1, wherein the shaft includes at least one lumen in fluid communication with the chamber.

6. The surgical instrument according to claim 3, wherein the fluid is selected from the group consisting of a gas and a liquid.

7. The surgical instrument according to claim 1, further comprising an inlet port defined in the handle assembly, wherein the inlet port is in fluid communication with the chamber.

8. The surgical instrument according to claim 7, wherein the inlet port includes a luer connector.

9. The surgical instrument according to claim 1, wherein the chamber is movable between a non-expanded position wherein the chamber is flush with the shaft and an expanded position.

10. The surgical instrument according to claim 1, wherein an outer surface of the chamber includes a plurality of protrusions.

11. The surgical instrument according to claim 1, wherein the chamber is made from at least one polymer material.

12. The surgical instrument according to claim 1, wherein the surgical instrument is an ablation device.

13. A surgical instrument comprising:
- a reusable handle assembly configured to connect to a source of energy;
- a shaft electrically coupled to the reusable handle assembly and extending from the reusable handle assembly, the shaft including a connection mechanism disposed at a distal end of the shaft;
- a limited-use component having a proximal end configured to releasably connect to the connection mechanism of the shaft for mechanically engaging and electrically coupling the shaft and the limited-use component for transmitting energy to treat tissue, the limited-use component forming a distal tip configured to penetrate tissue;
- an expandable chamber disposed on the shaft proximal to the limited-use component, wherein the expandable chamber is in fluid communication with a fluid source that is configured to selectively deliver fluid to the expandable chamber for expanding the expandable chamber to anchor the surgical instrument to tissue.

14. The surgical instrument according to claim 13, wherein the fluid source stores cooling fluid.

15. The surgical instrument according to claim 13, wherein the shaft includes at least one lumen defined therein in fluid communication with the expandable chamber.

16. The surgical instrument according to claim 13, wherein the fluid is selected from the group consisting of a gas and a liquid.

17. The surgical instrument according to claim 13, further comprising an inlet port defined in the handle assembly and in fluid communication with the expandable chamber, the inlet port including a luer connector, wherein the fluid source is a syringe configured for connection to the luer connector.

\* \* \* \* \*